United States Patent
Hokase

(10) Patent No.: US 6,787,134 B1
(45) Date of Patent: Sep. 7, 2004

(54) METHODS FOR PREVENTING/REMEDYING MASTITIS

(75) Inventor: Masanobu Hokase, Miyazaki (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/581,758

(22) PCT Filed: Dec. 18, 1998

(86) PCT No.: PCT/JP98/05749

§ 371 (c)(1),
(2), (4) Date: Jun. 16, 2000

(87) PCT Pub. No.: WO99/32144

PCT Pub. Date: Jul. 1, 1999

(30) Foreign Application Priority Data

Dec. 19, 1997 (JP) .............................................. 9/351220

(51) Int. Cl.⁷ ........................ A61K 38/46; A61K 38/43; C12N 9/16; C12N 9/00; A23K 1/17
(52) U.S. Cl. ..................... 424/94.6; 424/94.1; 424/442; 435/183; 435/196
(58) Field of Search ............................... 424/442, 94.6; 435/183, 196

(56) References Cited

U.S. PATENT DOCUMENTS 5,316,770 A * 5/1994 Edwards, Jr. ............... 424/442
5,612,055 A * 3/1997 Bedford et al. ............. 424/442
5,902,581 A * 5/1999 Clarkson et al.
6,132,716 A * 10/2000 Morgan et al.

FOREIGN PATENT DOCUMENTS

| | | |
|---|---|---|
| CN | 1135297 | * 11/1996 |
| EP | 359873 | 3/1990 |
| EP | 420428 | 4/1991 |
| JP | 2-83336 | 3/1990 |
| WO | WO 93/16175 | 8/1993 |
| WO | WO 98/54980 | 12/1998 |

OTHER PUBLICATIONS

Lyons, Biotechnology in the Feed Industry, Proceedings of Alltech's Eight Annual Symposium, 1992, pp., 1–22.*

* cited by examiner

*Primary Examiner*—Michael Meller
(74) *Attorney, Agent, or Firm*—Fitzpatrick, Cella, Harper & Scinto

(57) ABSTRACT

The present invention provides a novel method for preventing and treating mastitis in mammals and a composition for use in the method to prevent reduction in milk production caused by development of mastitis among livestock such as dairy cows, the invention being based on the finding that mastitis in mammals can be prevented and treated by administering phytase to the mammals.

5 Claims, 2 Drawing Sheets

US 6,787,134 B1

METHODS FOR PREVENTING/REMEDYING MASTITIS

FIELD OF THE INVENTION

The present invention relates to a method for preventing and treating mastitis, which has the highest incidence among genital diseases in mammals, by administering phytase alone or in admixture with feedstuff. The present invention further relates to a composition that contains phytase for preventing and treating mastitis in mammals.

BACKGROUND ART

Mastitis is an inflammation of the lactiferous duct system or mammary gland tissues caused by the invasion and proliferation of bacteria in the udder of a mammal. Once mammals get mastitis, the ability to synthesize milk is damaged by the inflammation. That is, the mammals start to secrete abnormal milk, and number of somatic cells, for example, leukocyte in the milk increases. Also, the mammary gland cells are damaged so that they become atrophied and the connective tissue increases, resulting in decreased lactation. In the dairy industry mastitis is known to stop the lactation, seriously damaging dairy production and management (Shigeru Hara, A Manual of Veterinary Medicine, published by Kodansha Ltd., 1988).

Moreover, an increase in the number of somatic cells due to mastitis decreases the commercial value of milk. Milk containing somatic cells above 500,000 cells/ml is discarded.

No effective method for preventing and treating mastitis has been established because of the difficulties in preventing and treating mastitis by pharmaceuticals or vaccination. Acute mastitis is treated by infusing liquid medicine containing antibiotics as active ingredient into the infected udder, injecting antihistamines or 5% glucose solution into the udder, or intra-arterially injecting antibiotics, such as kanamycin and ampicillin (Shigeru Hara, A Manual of Veterinary Medicine, Kodansha Ltd Publishers, 1988). Dairy cows received these treatments are discharged from milk production because of the problem of residual these medicine, which can significantly decrease dairy productivity. In addition, it was recently reported that oral administration of a pharmaceutical organic zinc preparation, for example zinc methionine sulfate suppressed an increase in the number of somatic cells, one symptom of mastitis (Feedstuffs, 57, 52, p11, 1985). However such administration has also been reported to have no efficacy against mastitis (Feedstuffs, 58, 12, p10, 1986).

Phytase is an enzyme that hydrolyzes phytic acid, an organic phosphorus compound that is difficult to digest, and promotes its absorption. Monogastric animals, such as swine and poultry have no phytase in their digestive tracts, so they cannot digest and absorb phytic acid.

In Japan, phytase has been designated as a feed additive (Japan Scientific Feeds Association, Japanese Standards of Feed Additives, 8$^{th}$ ed., 1996,). In other countries, phytase is widely used in feedstuff for swine and poultry farming. Many reports suggest that the addition of phytase into feedstuff for such animals could cause a significant increase in digestibility not only of phosphorus but also of calcium, zinc, proteins and the like (Proceedings of the 1996 Canadian Society of Animal Science Annual Meeting, Lethbrige, Alberta, Canada, A.W. Jongbloed et. al, 1996; British Journal of Nutrition, 64, 525–540, P. C. Simons et. al, 1990). However, there is no known preventive effect of phytase on mastitis.

On the other hand, since the microorganisms that produce phytase exist in their own ruminoreticulum (Cromwell et. al, J. Anim. Sci. 73, 2000–2008, G. L. 1995), the ruminants are believed to be able to decompose phytic acid themselves and administration of phytase is thought to have no effect on digestibility. Thus, phytase is not added to feedstuff for ruminants such as dairy cows.

The purpose of the present invention is to provide a novel method for preventing and treating mastitis in mammals and a composition for preventing and treating mastitis in order to prevent decrease in milk production due to mastitis in livestock, such as a dairy cow.

DESCRIPTION OF THE INVENTION

The present inventors have now found the administration of phytase can prevent and treat mastitis in mammals as a result of diligent research for solving the abovementioned problems.

The present invention relates to:
(1) A method for preventing and treating mastitis in mammals excluding humans, which comprises administering phytase to the mammals;
(2) The method for preventing and treating mastitis in mammals excluding humans of (1), which comprises administering 50 to 5,000 units of phytase per kg of dry feed matter,
(3) The method for preventing and treating mastitis of (1), wherein the mammal is a cow and the feed is formula feed for dairy cows;
(4) A composition for preventing and treating mastitis in mammals excluding humans, which comprises phytase;
(5) The composition for preventing and treating mastitis in mammals excluding humans of (4), which comprises phytase and formula feed; and
(6) The composition for preventing and treating mastitis in mammals excluding humans of (5), which comprises zinc methionine sulfate.

In this figure, the broken line means that feedstuff mixed with the composition C was given daily; the dotted line means that feedstuff without the composition C was given daily; and the arrow represents a day on which milk was collected and the number of somatic cells in the milk was measured.

Figure 2:
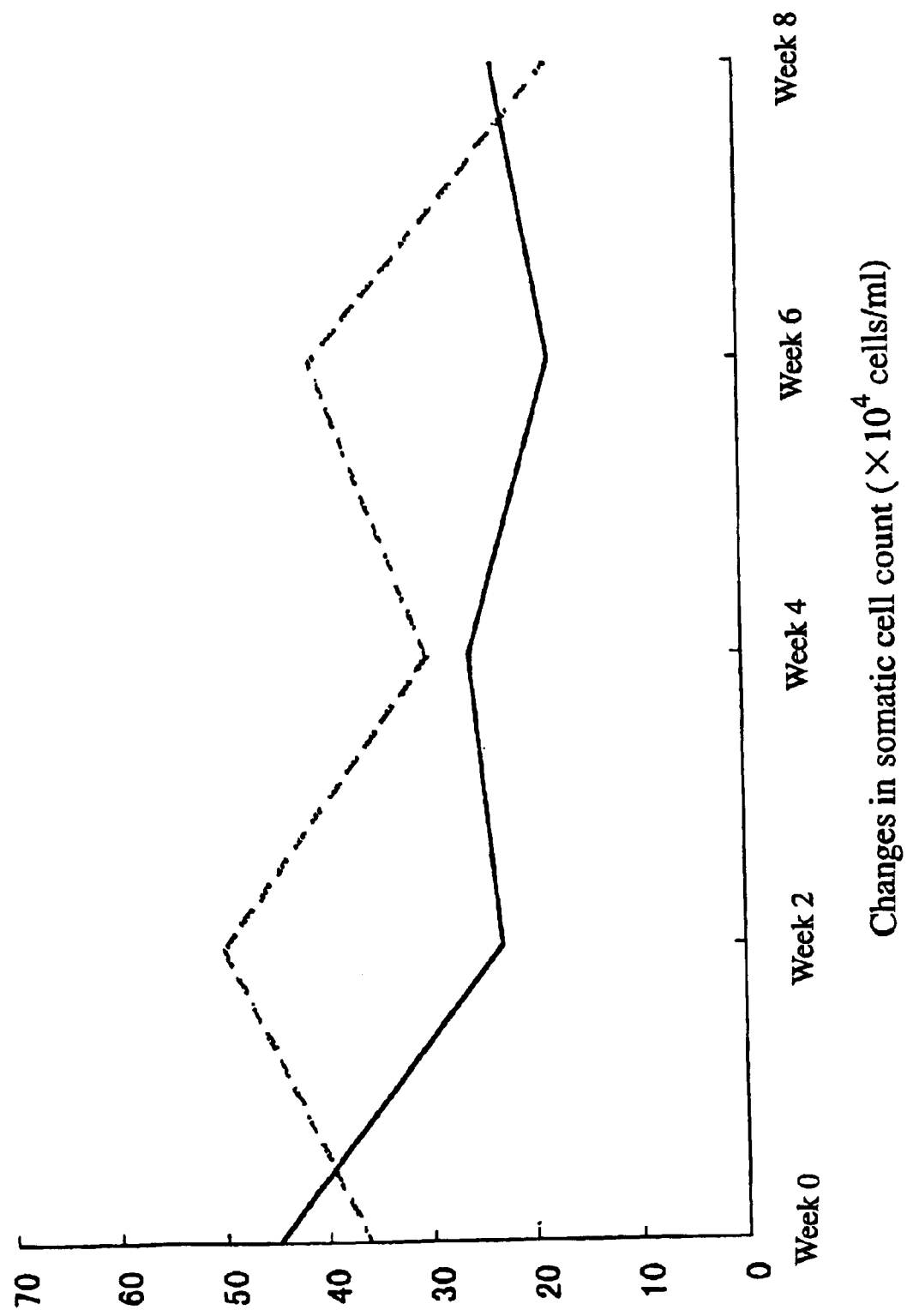

FIG. 2 shows changes in the number of somatic cells in the milk in the test. In this figure, the broken line represents the number of somatic cells in group A; and the dotted line represents the number of somatic cells in group B.

DESCRIPTION OF THE PREFERRED EMBODIMENTS

This invention will be further understood by reference to the Example set forth below. These examples are not intended to limit the scope of the appended claims.

Phytase (Enzyme number: 3.1.3.26 and 3.1.3.8) for use in this invention include those derived from microorganisms such as fungi, yeasts, and bacteria; those derived from plants such as barley, wheat, and rice bran; or those produced by a host cell, e.g., Escherichia coli, in which the phytase gene is introduced by standard genetic engineering technique. Preferable phytase is derived from fungi.

The dose of phytase to be administered for prevention and treatment of mastitis is 1 to 100 units/day/Kg of the weight of a mammal, preferably 10 to 50 units /day/Kg. When a composition containing phytase is mixed with feed for administration, 50 to 5,000 units of phytase, preferably 100 to 1,500 units, more preferably 250 to 750 units of phytase, is added per kg of dry feed.

The unit of phytase represents a unit of phytic acid decomposing activity as defined in the method for testing a phytic acid decomposing activity of the method for testing enzyme activity shown in attached table 2.5, "Methods for testing general feed additives" of A Ministerial Ordinance concerning Feed and Feed Additive Component Standard (Hajime Kameoka, ed. $8^{th}$ ed. Japan Scientific Feeds Association, 1996).

Mammals to which phytase is administered in this invention include mammals excluding humans, such as livestock e.g., cows, pigs, and goats; and pets, e.g., dogs and cats. Preferably cows are a ministered with phytase.

Methods for administering phytase to a mammal according to this invention include a method that comprises phytase adding directly to feedstuff and then administering the feedstuff containing phytase to the mammal, or a method that comprises phytase containing composition for prevention and treatment of mastitis and then orally administering the composition to the mammal.

Any feedstuff that is normally used for livestock may be used in this invention. Either individual feedstuff, roughage or formula feed may be employed. The individual feedstuff includes heated soybeans, cottonseeds, and soybeans. The roughage includes grass silage, alfalfa hay, beat pulp, grass hay, and hay. The formula feed a includes those for dairy cows, those for beef cows, those for fattening growing-finishing pigs, those for boars or breed sows, those for horses, those for goats, those for minks, and those for rabbits (Course of formula feed, the first volume, Ed. Compilation committee for course of formula feed, Tikusan Shuppan, 1980). Among of them, the formula feed for dairy cows can preferably be employed in this invention.

The formula feed for dairy cows is feedstuff wherein the above roughage; individual feedstuff; concentrated feedstuff e.g., cereals, brans, vegetable sake lees; inorganic feedstuff e.g., bone meal and calcium carbonate; and special feed e.g., vitamins, inorganic salts and amino acid additives are mixed appropriately according to well-known methods (Course of formula, feed, the first volume, Ed. Compilation committee for course of formula feed, Tikusan Shuppan, 1980).

Compositions of this invention for prevention and treatment of mastitis include those wherein phytase is contained in such as a veterinary pharmaceutical tablet or a veterinary pharmaceutical capsule; those wherein phytase is contained in a pet food; and those consisting of phytase and formula feed.

To administer the composition wherein phytase is contained in formula feed to mammals, the composition wherein phytase is contained in formula feed may be administered solely or the composition mixed with feedstuff e.g., roughage may be administered to mammals.

Any veterinary pharmaceutical tablet can be employed so far as it is normally used as drugs for animals. In addition to phytase as the active ingredient, these tablets can contain vehicles such as sugar (e.g., lactose and sucrose) and starch; binders such as gelatin and methyl cellulose; or lubricant such as talc and magnesium stearate.

Any veterinary pharmaceutical capsule can be employed so far as it is normally used as drugs for animals. These capsules are hard capsules for dairy use containing phytase as the active ingredient, which capsules may be filled with such as the above vehicles and the binders if necessary. Both these tablets and capsules for animals can be produced according to well-known methods (Pharmacy, Ed. Akinobu Otsuka et. al. Nankodo Co., Ltd. 1995).

Each tablet or capsule contains 100 to 20,000 units, preferably 1,000 to 10,000 units of phytase. The tablet or capsule containing phytase can be applied to both prevention and treatment of mastitis. Preferably they are applied to treatment as veterinary pharmaceuticals.

Any pet food can be employed for use in this invention so far as it is used for feeding companion animals, dogs and cats. These pet foods include those for dogs, such as dry food for dogs, purified feed for dogs, and semi-moist food for dogs; and pet foods for cats such as dry food for cats, purified feed for cats, and amino acid feed for cats. 100 g of pet food contains 5 to 500 units of phytase, preferably 25 to 100 units of phytase. Such pet food can be produced according to conventional methods for producing pet food (Course of formula feed, the first volume, Ed. Compilation committee for course of formula feed, Tikusan Shuppan, 1980).

The pet food containing phytase can be applied to both prevention and treatment for mastitis. Preferably this pet food is fed as a preventive food against mastitis so as to keep animal health.

The formula feed in the composition comprising phytase and formula feed is as described above. That is, the formula feed may contain feed additives as prescribed in the Law Concerning Safety Assurance and Quality Improvement of Feed (Japan), such as anti-deteriorating agents, e.g., calcium propionate and sodium propionate; vitamins; amino acids; minerals; or mixtures thereof. In the composition comprising phytase and formula feed, the preferable formula feed includes those for dairy cows.

The composition comprising phytase and formula feed contains 1,000 to 200,000 units, preferably 5,000 to 100,000 units of phytase per 100 g of the composition. This composition can be obtained according to well-known methods (Course of formula feed, the second volume, Ed. Compilation committee for course of formula feed, Tikusan Shuppan, 1979).

The composition comprising phytase and formula feed can applied to both prevention and treatment for mastitis. Preferably it is used as a composition for prevention of mastitis. Administering this composition before that dairy cows develope mastitis allows to effect dairy farming under good conditions where no cow suffers from mastitis.

Further, the above composition for prevention and treatment of mastitis may contain organs zinc, e.g., zinc methionine sulfate; inorganic zinc, e.g., zinc carbonate or zinc sulfate; manganese compounds, e.g., manganese carbonate or manganese sulfate; vitamins, e.g., vitamins A, D, and E; alfalfa meal; and flaked corns. Preferably the composition contains organo zinc or inorganic zinc, more preferably zinc methionine sulfate. To increase the palatability of feed, flavor may be given together with the composition.

For the timing and duration for administering the composition for prevention in this invention, administration of the composition preferably starts when an animal begins to milk and is kept during lactation. When an animal gets mastitis, the composition for prevention and treatment of mastitis may be given with feedstuff, or alternatively the composition may be administered, if necessary, in the form of a tablet or capsule for animals containing phytase.

EXAMPLES

Example 1

Feeding Trial of Dairy Cows Using Phytase

Each of Holstein dairy cows was fed daily with formula feed for dairy cows mixed with 30 g of a commercially available phytase (trade name: Phytase Kyowa, Kyowa Hakko Kogyo Co. Ltd., containing phytase derived from fungi at 500 units/g). This formula feed contains 28 kg of grass silage, 1.5 kg of alfalfa hay, 2 kg of beet pulp, 0.7 kg of heated soybeans, 1.2 kg of cottonseeds, 0.9 kg of soybean meal and 6 kg of concentrated feed. The feeding trial continued for 30 days using 65 cows in total in a free stall barn. Milk taken from all cows was combined together and then tested for its components every two weeks. The results are shown in Table 1.

TABLE 1

|  | 2 weeks before feeding | Start of feeding | After 2 weeks | After 4 weeks |
| --- | --- | --- | --- | --- |
| Average milk yield (L/day/cow) | 26.3 | 25.2 | 27.1 | 26.8 |
| Milk fat (%) | 4.0 | 4.2 | 4.2 | 4.3 |
| Milk protein (%) | 3.2 | 3.3 | 3.2 | 3.2 |
| Solid non-fat milk (%) | 8.9 | 8.8 | 9.1 | 9.0 |
| Number of somatic cells ($\times 10^4$ cells/ml) | 25.3 | 28.9 | 15.3 | 8.7 |

As shown in Table 1, before treated with phytase the cows were shown to have a number of somatic cells above $25 \times 10^4$ cells/ml exhibiting light symptoms of mastitis. However after the treatment the number of somatic cells clearly decreased, suggesting that mastitis could be prevented from its onset.

Example 2

Feeding Trails of Dairy Cows Using Phytase

Forty Holstein cows were divided into two groups of 20 cows each in cowhouses with tie stall barn. The first group was treated with phytase (test group) while the second group was untreated (control group). Each cow of both groups was fed daily with formula feed for dairy cows containing 15 kg of corn silage, 8 kg of grass hay, 3 kg of beet pulp, 4 kg of hay, and 8.0 kg of concentrated feed containing corn flakes, soybean meal, minerals, vitamins and the like. For the test group, 25 g of a commercially available phytase (trade name: Phytase Kyowa, Kyowa Hakko Kogyo Co., Ltd., containing phytase derived from fungi at 500 units/g) was sprinkled over the feed for administration. Each of cows was tested for the quality of its milk every month. The results are shown in Table 2.

TABLE 2

|  | Start of feeding | After 1 month | | After 2 months | |
| --- | --- | --- | --- | --- | --- |
|  | Test/Control | Test | Control | Test | Control |
| Average milk yield (L/day/cow) | 25.2 | 26.3 | 25.4 | 27.1 | 24.3 |
| Average milk fat (%) | 4.0 | 4.1 | 4.2 | 4.2 | 4.3 |
| Average milk protein (%) | 3.4 | 3.5 | 3.3 | 3.2 | 3.2 |
| Average solid non-fat milk (%) | 8.8 | 8.9 | 9.2 | 8.7 | 9.3 |
| Number of somatic cells ($\times 10^4$ cells/ml) | 30.2 | 12.1 | 35.2 | 8.6 | 42.1 |
| Number of cows treated against mastitis | 0 | 0 | 1 | 0 | 2 |

As shown in Table 2, before treated with phytase, tested cows group exhibit that the number of somatic cells is above $30 \times 10^4$ cells/ml and that symptoms of mastitis is light. In the test group treated with phytase, the number of somatic cells clearly decreased one month after the treatment. On the other hand in the control group untreated with phytase, the number of somatic cells is increased. That is, one cow and then two cows were diagnosed as having mastitis, 2 months and 3 months after the treatment, respectively. All of them were removed from the group for producing milk.

Example 3

Feeding Trials of Dairy Cows; Comparison of Phytase and Zinc Methionine Sulfate

Forty Holstein cows were divided into two groups of 20 cows each in cowhouses with tie stall barn. The first group was treated with phytase (test group) while the second group was treated with zinc methionine sulfate (control group). Each cow of both groups was fed daily with formula feed for dairy cows containing 15 kg of corn silage, 8 kg of grass hay, 3 kg of beet pulp, 4 kg of hay, and 8.0 kg of concentrated feed containing corn flakes, soybean meal, minerals, vitamins and the like. For the test group, each cow was treated daily with 25 g of a commercially available phytase (trade name:Phytase Kyowa, Kyowa Hakko Kogyo Co., Ltd., containing phytase derived from fungi at 500 units/g) sprinkled over the feed. For the control group, each cow was treated daily with 4 g of a commercially available zinc methionine sulfate formulation (Zinpro 40, Zinpro Corp.) sprinkled over the feed. Each cow of both groups was tested for the quality of its milk every month. The results are shown in Table 3.

TABLE 3

|  | Start of feeding | After 1 month | | After 2 months | |
| --- | --- | --- | --- | --- | --- |
|  | Test/Control | Test | Control | Test | Control |
| Average milk yield (L/day/cow) | 25.2 | 26.3 | 25.4 | 27.1 | 24.3 |
| Average milk fat (%) | 4.0 | 4.1 | 4.3 | 4.2 | 4.2 |
| Average milk protein (%) | 3.4 | 3.6 | 3.6 | 3.1 | 3.2 |
| Average solid non-fat milk (%) | 8.8 | 8.7 | 9.2 | 8.8 | 9.0 |
| Number of somatic cells ($\times 10^4$ cells/ml) | 35.2 | 15.1 | 25.3 | 8.6 | 12.1 |

As shown in Table 3, before treated with phytase, tested cows groups exhibit that the number of somatic cells is $30 \times 10^4$ cells/ml and that symptoms of mastitis is light. In the test group treated with phytase, the number of somatic cells clearly decreased one month after the treatment. In the control group treated with zinc methionine sulfate, the number of somatic cells also decreased. However, the addition of phytase was significantly more effective than zinc methionine sulfate.

Example 4

Composition A for Preventing Mastitis

Composition A for preventing mastitis was formed by adding 200 g of phytase (trade name:Phytase Kyowa, Kyowa Hakko Kogyo Co., Ltd., containing phytase derived from fungi at 500 units/g) to 1 kg of a commercially available formula feed for dairy cows containing feed additives listed in Table 4 below (trade name: CELLCUT-2, Kyowa Hakko Kogyo Co., Ltd.).

TABLE 4

| Feed additive contained | Effective component | Content (per kg feed) |
| --- | --- | --- |
| Vitamin A Oil | As vitamin A | 2500.0 kIU |
| Vitamin D3 Oil | As vitamin D3 | 500.0 kIU |
| Dry formed Vitamin E | As vitamin E | 1000.0 mg |
| Vitamin K3 | Menadione sodium sulfite | 300.0 mg |
| Vitamin B1 | Thiamin sulfate | 300.0 mg |
| Vitamin B2 | Riboflavin | 600.0 mg |
| Vitamin B6 | Pyridoxine hydrochloride | 1500.0 mg |
| Vitamin B12 | Cyanocobalamin | 2.0 mg |
| Calcium pantothenate | Pantothenic acid | 6000.0 mg |
| Nicotinamide | Niacin | 60000.0 mg |
| Choline chloride | | 25000.0 mg |
| Manganese carbonate | As Mn | 1200.0 mg |
| Iron sulfate (dry) | As Fe | 1500.0 mg |
| Cobalt sulfate | As Co | 5.0 mg |
| Zinc carbonate | As Zn | 1200.0 mg |
| Calcium iodate | As I | 19.5 mg |
| Magnesium Carbonate | As Mg | 8000.0 mg |
| Zinc MET sulfate | Zinc methionine sulfate | 30000.0 mg |
| | As Zn | 6000.0 mg |
| | As MET | 12000.0 mg |
| Sweetener | | q.s. |
| Balance | | Defatted rice bran, Oil meal |

Example 5

Composition B for Preventing Mastitis

Composition B for preventing mastitis was formed by adding 200 g of phytase (trade name:Phytase Kyowa, Kyowa Hakko Kogyo Co., Ltd., containing phytase derived from fungi at 500 units/g) to 1 kg of a commercially available formula feed for dairy cows containing feed additives listed in Table 5 below (trade name: Supervitamin Supplement, Kyowa Hakko Kogyo Co., Ltd.).

TABLE 5

| Feed additive contained | Effective component | Content (per kg feed) |
| --- | --- | --- |
| Vitamin A Oil | As vitamin A | 2500.0 kIU |
| Vitamin D3 Oil | As vitamin D3 | 500.0 kIU |
| Dry formed Vitamin E | As vitamin E | 1000.0 mg |
| Vitamin K3 | Menadione sodium sulfite | 300.0 mg |
| Vitamin B1 | Thiamin sulfate | 300.0 mg |
| Vitamin B2 | Riboflavin | 600.0 mg |
| Vitamin B6 | Pyridoxine hydrochloride | 1500.0 mg |
| Vitamin B12 | Cyanocobalamin | 2.0 mg |
| Calcium pantothenate | Pantothenic acid | 6000.0 mg |
| Nicotinamide | Niacin | 60000.0 mg |
| Choline chloride | | 25000.0 mg |
| Manganese carbonate | As Mn | 1200.0 mg |
| Iron sulfate (dry) | As Fe | 1500.0 mg |
| Cobalt sulfate | As Co | 5.0 mg |
| Zinc carbonate | As Zn | 1200.0 mg |
| Calcium iodate | As I | 19.5 mg |
| Magnesium Carbonate | As Mg | 8000.0 mg |
| Sweetener | | q.s. |
| Balance | | Defatted rice bran, Oil meal |

Example 6

Composition C for Preventing Mastitis

Composition C for preventing mastitis was formed by adding 400 g of phytase (trade name:Phytase Kyowa, Kyowa Hakko Kogyo Co., Ltd., containing phytase derived from fungi at 500 units/g) to 1 kg of a commercially available formula feed for dairy cows containing feed additives listed in Table 6 below (trade name: CELLCUT-I, Kyowa Hakko Kogyo Co., Ltd.).

TABLE 6

| Feed additive contained | Effective component | Content (per kg feed) |
| --- | --- | --- |
| Vitamin A Oil | As vitamin A | 5000.0 kIU |
| Vitamin D3 Oil | As vitamin D3 | 1000.0 kIU |
| Dry formed Vitamin E | As vitamin E | 4000.0 mg |
| Manganese carbonate | As Mn | 230.0 mg |
| Zinc carbonate | As Zn | 700.0 mg |
| Zinc MET sulfate | Zinc methionine sulfate | 60000.0 mg |
| | As Zn | 12000.0 mg |
| | As MET | 24000.0 mg |
| Alfalfa meal | | 10000.0 mg |
| Sweetener | | q.s. |
| Balance | | Defatted rice bran, Oil meal |

Example 7

Method for Preventing Mastitis Using Composition C

For 50 dairy cows per group, standard feed with or without the composition C (5 kg/day) from Example 6 were fed alternately every two weeks.

Figure 1:
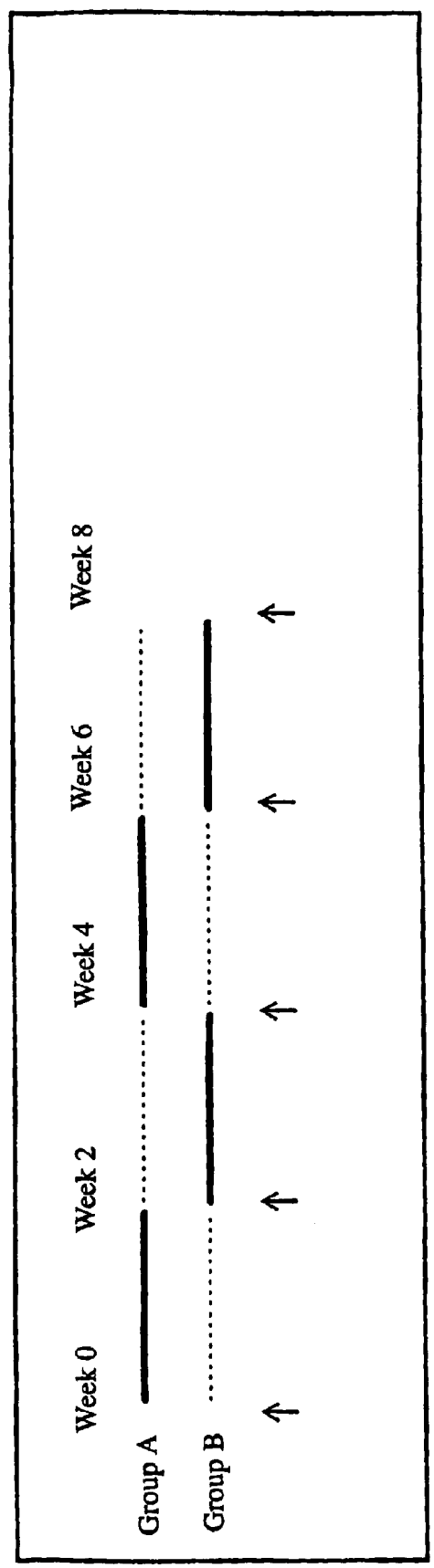
FIG. 1 shows the feed schedule for dairy cows according to the switch back method.

The cows fed with the feed were divided into two groups, A and B. Feeding was started with the feed containing composition C for group A while the feed without composition C for group B, according to the switchback procedure shown in FIG. 1.

After start of the feeding, milk was taken from each cow of both groups every two weeks. Then the milk was combined together for each group to measure the number of somatic cells in the milk, an indicative of mastitis. The results are shown in Table 7 and FIG. 2.

TABLE 7

| | Week 0 | Week 2 | Week 4 | Week 6 | Week 8 |
| --- | --- | --- | --- | --- | --- |
| Group A | 45 | 23 | 26 | 18 | 23 |
| Group B | 36 | 50 | 30 | 41 | 18 |

(Unit: ×10$^4$ cells/ml)

As shown in Table 7 and FIG. 2, both of the groups were shown to have an ability to inhibit mastitis after about 8 weeks of the study because they exhibited decrease in the number of somatic cells compared to the results obtained before start of the study.

The results of the study from week 0 to week 2 suggest that the number of somatic cells decreased in group A fed with the feed containing composition C whereas it increased in group B fed only with the standard feed. Accordingly, the effective prevention against mastitis could also be achieved by incorporating composition C into feed.

Industrial Applicability

According to the present invention, there are provided the method and the composition for preventing and treating mastitis in mammals (excluding humans).

All publications, patents and patent applications cited herein are incorporated herein by reference in their entirety.

What is claimed is:

1. A method for treating a lactating cow that suffers from mastitis, comprising:

administering to the lactating cow which suffers from mastitis a therapeutically effective amount of phytase.

2. The method according to claim 1, which comprises administering feedstuff containing 50 to 5,000 units phytase per kg of dry feed to said lactating cow matter.

3. The method according to claim 2, wherein the feedstuff comprises formula feed.

4. The method according to claim 2, wherein the feedstuff further comprises zinc methionine sulfate.

5. The method according to claim 1, wherein the concentration of somatic cells in the milk of the lactating cow is greater than $2.5 \times 10^5$ cells/ml prior to treatment.

* * * * *